United States Patent [19]

Stofac

[11] Patent Number: 5,030,575
[45] Date of Patent: Jul. 9, 1991

[54] APPARATUS FOR PRESERVING AND TESTING LIVING EYE TISSUES

[76] Inventor: Robert L. Stofac, 10180 W. Asbury Ave., Lakewood, Colo. 80227

[21] Appl. No.: 567,265

[22] Filed: Aug. 14, 1990

[51] Int. Cl.$^5$ .............................................. C12M 3/00
[52] U.S. Cl. ..................................... 435/296; 436/176
[58] Field of Search ................... 435/1, 240.22, 240.23, 435/240.24, 240.25, 283, 293, 296; 436/176, 174; 422/292, 307, 294

[56] References Cited

U.S. PATENT DOCUMENTS 4,296,205  10/1981  Verma ................................. 435/296
4,334,028  6/1982  Carver ................................. 435/296

Primary Examiner—David L. Lacey
Assistant Examiner—Thomas E. Daley
Attorney, Agent, or Firm—Klaas & Law

[57] ABSTRACT

An apparatus for preserving and conducting chemical tests on corneal tissues. The apparatus consists of a chamber having a medial portion with a port therethrough. Operatively attached to the port is a system for retaining the cornea in position. Placed over the port and in direct contact with the cornea is a cover member of non-abrasive, biologically compatible material. A nutrient supply conduit delivers liquid nutrients to the cover member from an external source. The nutrients are imparted to the cornea through direct contact between the cornea and the cover member. Residual nutrients are collected in a reservoir secured to the chamber beneath the port. The reservoir is drained using a waste conduit. Also, the chamber is filled with nutrients so that the inner surface of the cornea is sustained. As a result, the corneal tissues are maintained in a living state.

15 Claims, 2 Drawing Sheets

APPARATUS FOR PRESERVING AND TESTING LIVING EYE TISSUES

BACKGROUND OF THE INVENTION

The present invention generally relates to the storage, preservation, and testing of living eye tissues, and more particularly to a system for maintaining eye tissues in a living state over extended periods of time for testing purposes.

The development of new cosmetics, drugs, and other chemical products requires that these materials be extensively tested before public introduction. Specifically, the materials must be tested to determine if they produce any adverse reactions during contact with human tissues. This is especially important with respect to eye tissues (e.g. the transparent portion of the eye known as the cornea). Cosmetics and other chemical products which potentially come in contact with eye tissues during normal use must be thoroughly tested to ensure a sufficient degree of safety.

Current testing procedures involving cosmetics, chemicals, and eye tissues require the use of live animal subjects. These in vivo procedures are the subject of considerable controversy since they often involve direct physical damage to the eye tissues in a live, unanesthetized animal. A difficult conflict therefore exists between the need to conduct vital precautionary research, and the prevention of cruelty to animals. The present invention eliminates this conflict, and involves an apparatus which enables living eye tissues to be preserved in vitro and tested without the use of live animal subjects. Specifically, the apparatus comprises an in vitro system which allows the preservation and simultaneous testing of eye tissues from swine, sheep, rabbit, or bovine specimens obtained from meat processing plants and the like. In addition, the apparatus may also be used to preserve and test human eye tissues which become available during surgical procedures, or which have been rejected for human transplantation. By preserving and testing eye tissues from non-living subjects, the need for live animal testing is substantially eliminated. The present invention therefore represents an advance in the art of tissue preservation/testing and offers numerous benefits, as described in detail below.

SUMMARY OF THE INVENTION

It is an object of the present invention to provide a method and apparatus for preserving eye tissues in vitro so that such tissues may be tested for reactions to chemicals, drugs, biologicals and the like.

It is another object of the invention to provide a method and apparatus for preserving and testing eye tissues which eliminates the need for destructive tissue tests on live animal subjects.

It is a further object of the invention to provide a method and apparatus for preserving and testing eye tissues which is especially effective with respect to the anterior tissues of the eye (e.g. the cornea).

It is a still further object of the invention to provide a method and apparatus for preserving and testing eye tissues which is easy to use and requires a minimal number of operating components.

It is an even further object of the invention to provide a method and apparatus for preserving and testing eye tissues which prevents physical damage to the tissues and provides the tissues with a constant supply of nutrient materials.

In accordance with the foregoing objects, a method and apparatus is disclosed which maintains eye tissues in a living state over extended periods of time. The eye tissues may then be used for in vitro testing, thereby eliminating the use of live animal subjects. Specifically, an apparatus is disclosed which consists of a chamber having a medial portion with a port therethrough. A cornea-containing tissue specimen from a human or animal subject is placed over the port and secured in position using a specialized retaining assembly. Positioned over the port and in direct contact with the cornea is a cover member of non-abrasive material which is biologically compatible with the corneal tissues. In a preferred embodiment, the cover member consists of a sheet of omentum or conjunctival tissue from a human or animal source sized to fit over the port and the tissue specimen. In an alternative embodiment, the cover member may consist of a species-specific fibroblast/fibrocyte monolayer tissue culture specimen. The upper edge of the cover member is supplied with liquid nutrient materials delivered from an external source through a nutrient supply conduit operatively secured to the chamber. The nutrient supply conduit delivers liquid nutrient materials directly to the inner surface of the cover member, thereby wetting the surface of the cover member with nutrient materials. As the liquid nutrient materials flow downwardly along the inner surface of the cover member, they come in contact with the cornea, thereby moistening the outer surface of the cornea and maintaining it in a living state. Excess liquid nutrient materials which drain from the cover member are collected in an elongate reservoir secured to the chamber directly beneath the port and the cover member. Liquid nutrient materials within the reservoir are subsequently drained therefrom using a waste conduit. In this manner, the eye tissues are effectively preserved either prior or during testing.

In addition, the chamber of the present invention is designed to retain a supply of liquid nutrient materials therein in order to maintain and preserve the inner surface of the cornea. The liquid nutrient materials within the chamber gain access to the inner surface of the cornea through the port to which the cornea is attached. In a preferred embodiment, the liquid nutrient materials within the chamber are maintained at a specified temperature level using a selected heating system.

These and other objects, features, and advantages of the invention shall be described below in the following Detailed Description of Preferred Embodiments and Brief Description of the Drawings.

BRIEF DESCRIPTION OF THE DRAWINGS

Illustrative and presently preferred embodiments of the invention are shown in the accompanying drawings in which.

DETAILED DESCRIPTION OF THE PREFERRED EMBODIMENTS

Figure 1:
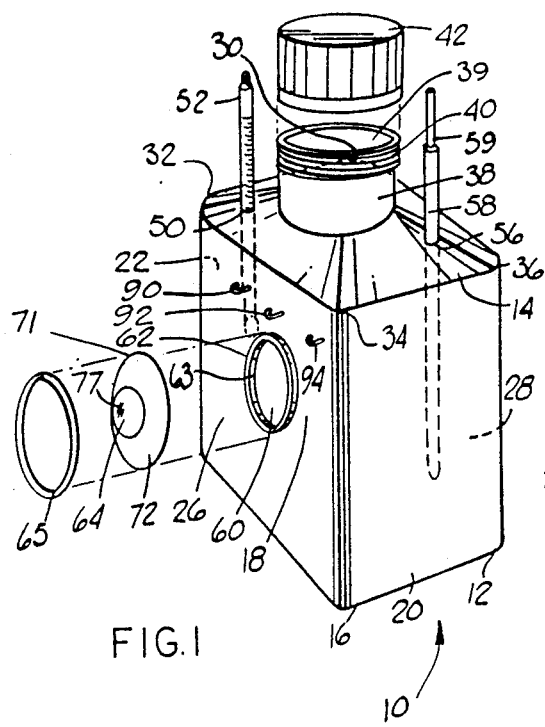
FIG. 1 is a perspective view of an apparatus produced in accordance with the present invention prior to the mounting of a cornea-containing tissue specimen thereto.
Figure 2:
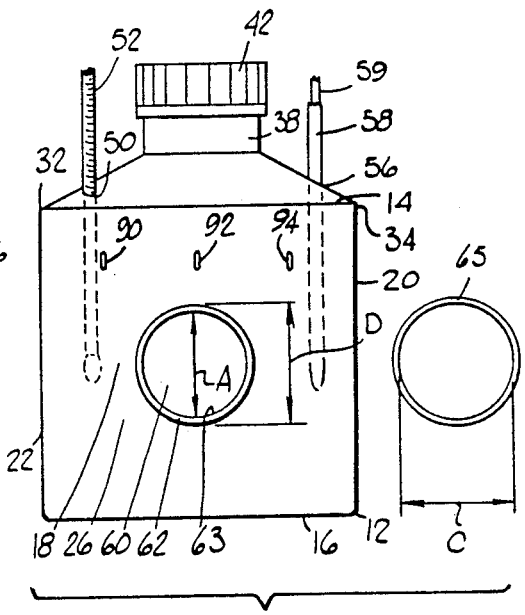
FIG. 2 is a front view of the apparatus of FIG. 1 prior to the mounting of a cornea-containing tissue specimen thereto.
Figure 3:
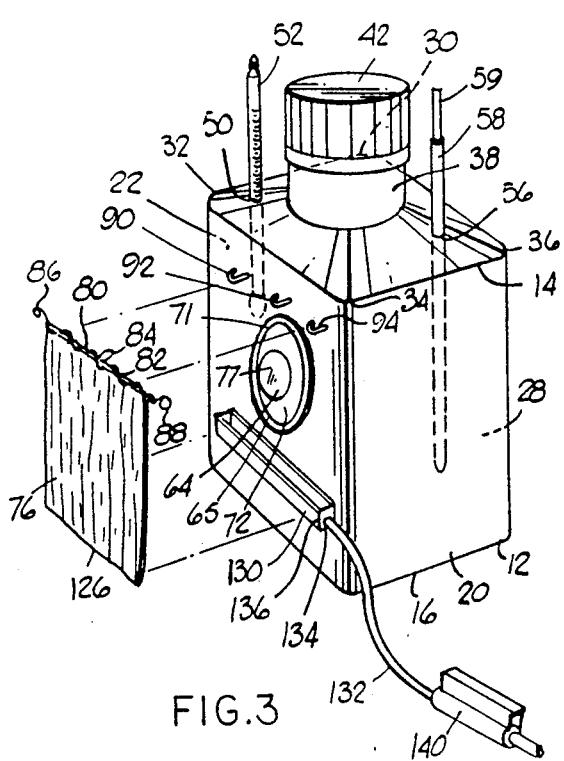
FIG. 3 is a perspective view of the apparatus of FIG. 1 having a cornea-containing tissue specimen secured thereto.

The present invention involves an apparatus and method designed to preserve living eye tissues so that in vitro tests may be conducted on the tissues. Use of the invention described herein offers substantial benefits, including the elimination of destructive tissue testing on live animal subjects.

With reference to FIGS. 1-6, a tissue preservation apparatus 10 produced in accordance with the present invention is illustrated. The apparatus 10 includes a chamber 12 having a top portion 14, a bottom portion 16, and a medial portion 18 therebetween. In a preferred embodiment, the chamber 12 is substantially rectangular in configuration having sides 20, 22 which are parallel to each other, a front panel 26 and a rear panel 28. In this configuration, the top portion 14 of the chamber 12 includes four corners 30, 32, 34, 36 and is slightly pyramid-shaped, as illustrated. However, the chamber 12 may be externally configured in a different manner, and the present invention shall not be limited to the rectangular construction illustrated in FIGS. 1-6. It is also preferred that the chamber 12 be manufactured of an inert, transparent plastic such as polyethylene, although glass or other materials may be used.

The top portion of the chamber 12 further includes a neck 38 which is equidistant from the corners 30, 32, 34, 36. The neck 38 has an opening 39 therethrough and a threaded section 40. The threaded section 40 is adapted to threadably engage a removable sealing member or lid 42 having a complementary internal threaded section (not shown).

In a preferred embodiment, the chamber 12 is of rectangular construction as noted above, and is about 6.5 cm long, 6.5 cm wide, and 10.0 cm tall with a fluid capacity of about 500 cc of liquid nutrient materials. The liquid nutrient materials are supplied to the chamber 12 through the opening 39 in the neck 38 which is thereafter sealed using the lid 42. A preferred liquid nutrient material consists of a product known in the art as "Minnesota System Medium" which includes numerous metabolites, salts, and buffers (e.g. L-glutamine, decomplemented calf serum (5%), fetal calf serum (5%), chondroitin sulfate, and gentamicin sulfate). If desired, various growth stimulators may be added including fibronectin and epidermal growth factor (E.G.F). It also has a substantially neutral pH (e.g. 7.4). When used with the invention described herein, Minnesota System Medium is capable of keeping corneal tissues alive in vitro at human physiological temperature levels (about 98° F.) over about a 28 day period. Minnesota System Medium is specifically designed to support cell growth, adhesion, and migration. It is described in greater detail in Lindstrom, R. L., "Minnesota System Corneal Preservation," *British Journal of Ophthalmology* 70:47-54 (1986). However, the present invention shall not be limited to the use of Minnesota System Medium only, and other appropriate media materials known in the art may be used.

The top portion 14 of the chamber 12 further includes a first opening 50 which is sized to allow the passage of a thermometer 52 known in the art therethrough. In the embodiment of FIGS. 1-6, the opening 50 is about ⅜ inch in diameter, and is positioned adjacent corner 32 of the top portion 14 as illustrated. The thermometer 52 is designed for immersion within the liquid nutrient materials in the chamber 12 so that the temperature thereof may be monitored.

The top portion 14 of the chamber 12 also includes a second opening 56 adjacent corner 36 which is sized to allow the passage of a heating unit 58 therethrough. In the embodiment of FIGS. 1-6, the opening 56 is between about ⅜ inch to 1.0 inch in diameter. The heating unit 58 preferably consists of a tubular, glass-encased heating coil of the type normally used in tropical fish aquariums which is well known in the art. The heating unit 58 is connected to an external power source (not shown) using a cord 59. It is immersed within the liquid nutrient materials in the chamber 12 so that the materials may be heated to the desired temperature noted above (e.g. 98° F.).

In an alternative embodiment (not shown), an external heating system may be used to maintain the liquid nutrient materials at a desired temperature within the chamber 12, including but not limited to a conventional hot plate apparatus.

The medial portion 18 of the chamber 12 as shown in FIG. 1 includes a cornea-receiving port 60 through the front panel 26. The port 60 is substantially circular in configuration, and includes an annular raised flange 62 surrounding the peripheral edge 63 of the port 60. The diameter "A" of the port 60 will vary depending on the origin of the corneal tissue specimen, although it will typically range from about 2.0 cm for human cornea-containing tissue specimens to about 4.0 cm for bovine specimens. However, the diameter "A" of the port 60 (FIG. 2) must be slightly larger than the diameter "B" (FIG. 7) of the cornea 64 with which it is used. For example, if a bovine specimen is used (having a cornea which is approximately 3.0 cm in diameter), the port 60 should have a diameter "A" of about 4.0 cm. The reason for this difference in size will be explained in greater detail below.

Also provided in accordance with the invention is an annular retaining ring 65 shown in FIGS. 1-3 and 6. The retaining ring 65 is designed to securely fit over the flange 62 (FIGS. 3 and 6) in order to firmly engage the cornea-containing tissue specimen therebetween. To accomplish this, the ring 65 should have an internal diameter "C" (FIG. 2) slightly less than the diameter "D" of the flange 62. To enable placement of the ring 65 over the flange 62, the ring 65 is preferably manufactured of a resilient, stretchable material (e.g. rubber) which is able to deform so that attachment of the ring 65 may be accomplished.

Figure 7:
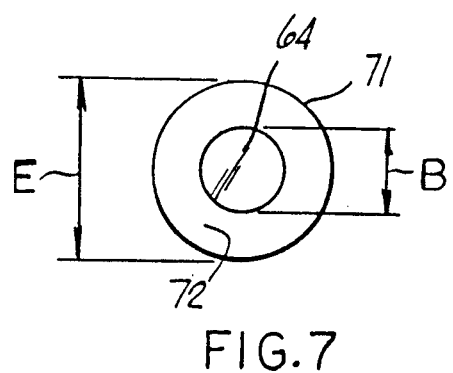
FIG. 7 is a front view of a cornea-containing tissue specimen adapted to be retained and preserved by the present invention.

To prevent damage to the cornea 64 during attachment, the entire cornea-containing tissue specimen 71 shown in FIG. 7 (normally characterized as the "anterior segment" of the eye) should be surgically removed from the donor so that an annular section of scleral tissue 72 surrounds the cornea 64 as illustrated in FIG. 7. As noted above, the diameter "B" of the cornea 64 should be less than the diameter "A" of the port 60 so that the cornea 64 is positioned entirely within the port 60 (e.g. centered).

Figure 6:
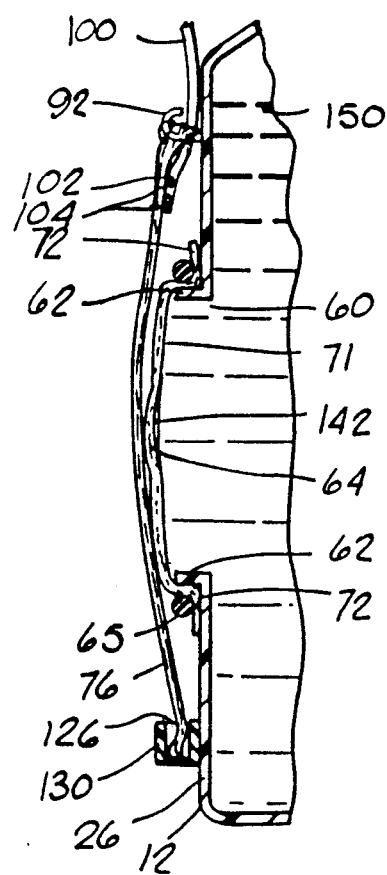
FIG. 6 is a partial sectional view taken along line 6—6 of FIG. 5.

To secure the specimen 71 in position over the port 60, the overall diameter "E" of the specimen 71 shown in FIG. 7 (including the annular section of scleral tissue 72) should be greater than the diameter "D" of the flange 62 so that the specimen 71 slightly overlaps the edges of the flange 62 when positioned thereon. Thereafter, the ring 65 is positioned on the flange 62 and secured thereto, with the overlapping portions of scleral tissue 72 being fixedly secured between the ring 65 and the flange 62 (FIG. 6). As a result, the mounted specimen 71 will be secured so that the cornea 64 is centered entirely within the port 60. Mounting of the specimen 71 in this manner prevents damage to the delicate cornea 64 which is then preserved as described below.

Figure 4:
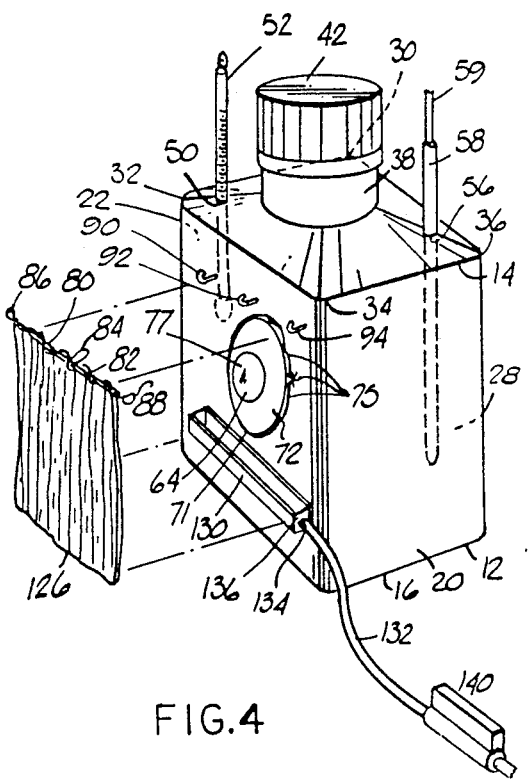
FIG. 4 is a perspective view of the apparatus of FIG. 1 having a cornea-containing tissue specimen secured thereto using an alternative attachment method.

In an alternative embodiment illustrated in FIG. 4, the specimen 71 is positioned on the flange 62 as described above. However, the ring 65 is not used. Instead, a portion of #00 black silk suture 75 is tied around the flange 62, securing the specimen 71 therebetween as shown in FIG. 4. The suture 75 is then suitably tied in order to maintain the specimen 71 in position.

After mounting of the specimen 71 is completed, a cover member 76 (FIGS. 3-6) is positioned over the port 60 and against the outer surface 77 (e.g. the epithelial side) of the cornea 64. The cover member 76 should be made of a material which is thin, non-abrasive, and biologically compatible with the cornea 64. For the purposes described herein, the term "biologically compatible" means that the cover member 76 shall be made of a material which does not cause any adverse chemical/biological reactions with the corneal tissues being preserved. An exemplary material for this purpose is a thin sheet of omentum tissue from a human or animal specimen. Omentum tissue consists of mesothelial cells derived from the inner linings of the peritoneum or supporting abdominal viscera. It is relatively strong (tear-resistant), substantially non-abrasive, and biologically compatible (in most cases) with eye tissues. Omentum tissue closely approximates the inner lining of human or animal eyelids, and is desirable for this reason. The omentum tissue used in the present invention does not have to come from the same source as the corneal specimen being preserved. However, if possible, a greater degree of biological compatibility exists if the corneal specimen and omentum tissue come from the same species.

In an alternative embodiment, the cover member 76 may consist of human or animal conjunctival tissue. Conjunctival tissue consists of the mucous membrane that covers the eye and lines the eyelids. In a further alternative embodiment, a tissue culture of fibroblasts and fibrocytes harvested in a monolayer may be used as the cover member 76. Again, a greater degree of biological compatibility exists if the corneal specimen and the tissue culture come from the same species. Finally, synthetic cover members 76 may be used, as long as they are non-abrasive and biologically compatible with the corneal specimen. Exemplary synthetic cover members 76 include those manufactured of polymers used in the production of soft contact lenses (e.g. materials sold under the name "Polymacon").

The ultimate size of the cover member 76 may be varied, as long as it entirely covers the port 60 and cornea 64. However, in a preferred embodiment, the cover member 76 is about 30 mm × 30 mm.

With continued reference to FIGS. 3-6, the cover member 76 is secured in position on the front panel 26 of the chamber 12. Specifically, the upper longitudinal edge 80 of the cover member 76 includes a portion of #000000 black silk suture 82 which is woven therethrough as illustrated. In the present embodiment, the suture 82 is woven so that an inner loop 84 is formed in the middle of the longitudinal edge 80. Likewise, the suture 82 is woven so that end loops 86, 88 are formed at each end of the longitudinal edge 80.

To secure the cover member 76 in position, three hooks 90, 92, 94 are provided on the front panel 26 of the chamber 12 above the port 60. The hooks 90, 92, 94 may be integrally formed during manufacture of the chamber 12, or secured thereto using adhesives or the like. To attach the cover member 76 to the chamber 12, the inner loop 84 is secured to the hook 92, with the end loops 86, 88 being secured to the hooks 90, 94 respectively. In this manner, the cover member 76 is properly oriented over the port 60. In a preferred embodiment, when the suture 82 is woven into the cover member 76, the loops 84, 86, 88 should be positioned so that they will be properly aligned with the hooks 90, 92, 94. Also, the distance from hook 90 to hook 94 should be substantially equal to the overall length of the cover member 76 so that proper mounting of the cover member 76 may take place.

In accordance with the present invention, the number and orientation of the hooks and loops may be suitably varied. It should also be noted that other methods may be used to secure the cover member 76 in position over the port 60, and the present invention shall not be limited to the method described above.

Figure 5:
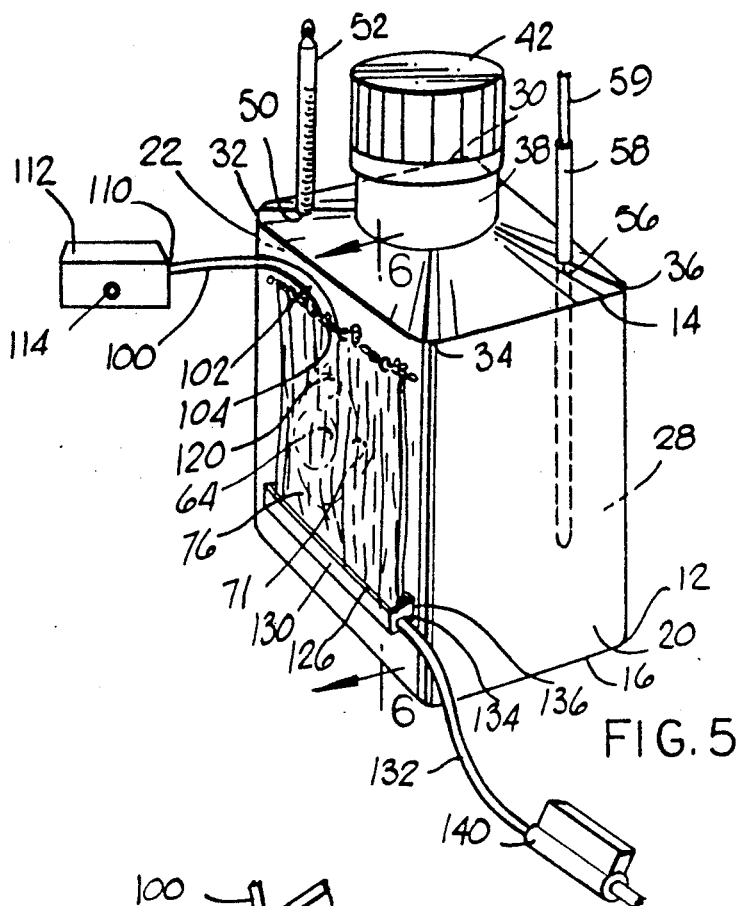
FIG. 5 is a perspective view of the apparatus of FIG. 1 having a cornea-containing tissue specimen secured thereto wherein a cover member is secured in position over the specimen.

With reference to FIGS. 5-6, a nutrient supply conduit 100 is illustrated. The supply conduit 100 has a first end 102 which is frictionally engaged between the cover member 76 and the front panel 26 of the chamber 12. If needed, the end 102 of the conduit 100 may be maintained in position using a portion of surgical tape or the like (not shown) to attach the conduit 100 to the front panel 26 of the chamber 12 at a position above the cover member 76. When secured as described above, the first end 102 of the conduit 100 directly touches the cover member 76 (FIG. 6).

In a preferred embodiment, the supply conduit 100 is manufactured of flexible plastic or rubber, with the end 102 including a plurality of perforations 104 as shown in FIGS. 5-6. The opposite end 110 of the supply conduit 100 is attached to an external source 112 of liquid nutrient materials. The liquid nutrient materials (e.g. Minnesota System Media supplemented with growth stimulators such as fibronectin or E.G.F.) are delivered through the conduit 100 by gravity (e.g. elevation of the external source 112 above the chamber 12) or by an optional in-line pump known in the art (not shown). In either embodiment, it is preferred that a liquid nutrient flow rate of about 1-2 ml/hour be maintained. Also, the source 112 may have an optional heater unit 114 therein in order to maintain the liquid nutrient materials delivered through conduit 100 at a selected temperature (e.g. 98° F.). In operation, the liquid nutrient materials are delivered from the source 112 into the end 102 of the conduit 100. The materials pass outwardly through the perforations 104 and run downwardly along the inner surface 120 of the cover member 76. Since the cover member 76 comes in contact with the specimen 71, the liquid nutrient materials passing along the inner surface 120 of the cover member 76 bathe the cornea 64. This keeps the outer surface 77 of the cornea 64 moist and supplied with necessary metabolites.

Residual liquid nutrient materials are collected at the lower longitudinal edge 126 of the cover member 76 which is positioned adjacent an outwardly extending trough or elongate reservoir 130 operatively secured to the front panel 26 of the chamber 12 below the port 60. The residual liquid nutrient materials are received within the reservoir 130 and flow outwardly therefrom by gravity through a waste conduit 132 preferably manufactured of rubber, plastic, or other flexible material. The waste conduit 130 is fitted within an orifice 134 in end 136 of the reservoir 130 as shown in FIG. 5. The waste conduit 130 optionally includes an in-line ultraviolet lamp 140 known in the art designed to disinfect the residual liquid nutrient materials and to prevent retrograde contamination.

Finally, as noted above, the chamber 12 is filled with liquid nutrient materials through the opening 39 in the neck 38. The liquid nutrient materials within the chamber 12 are designed to moisten and preserve the inner surface 142 (e.g. the endothelium) of the cornea 64 as shown in FIG. 6. The chamber 12 is preferably filled to a level designated by reference number 150 in FIG. 6 which is above the port 60. This enables the entire inner surface 142 of the cornea 64 to be immersed in the liquid nutrient materials. In addition, leakage of the liquid nutrient materials through the port 60 is prevented by the secure engagement of the specimen 71 against the flange 62 using the ring 65 or suture 75 as described above. If there is concern regarding contamination of the liquid nutrient materials within the chamber 12, the materials may be periodically or continuously exchanged using a series of additional conduits in combination with a slow drive sigmoid pump (not shown) or other pump assembly known in the art.

The present invention represents a substantial advance in the art of eye tissue preservation. As indicated herein, the invention enables corneal specimens to be preserved in a living state for substantial periods of time. This eliminates the need to conduct destructive chemical testing on eye tissues of living animal specimens. When chemical tests are conducted using the apparatus described herein, selected agents are administered to the mounted corneal specimen, followed by placement of the cover member 76 against the specimen and introduction of the liquid nutrient materials. At any time during the testing procedure, the cover member 76 may be lifted to inspect the cornea either grossly or microscopically using a standard or portable slit lamp microscope. Non-toxic vital dyes such as fluorescein or Rose Bengal may be used to measure the extent of either epithelial healing or progressive destruction. Also, the invention can be used to retain, preserve, and test eye tissues which have been infected by inoculation with various infectious agents including bacteria, viruses, and chlamydia. The apparatus described herein is small enough to be covered with a bell jar or the like to maintain sterility. Sterile conditions are also maintained by using disposable latex gloves and sterile forceps to lift the cover member. However, it is important to note that the invention is also designed to preserve corneal tissues before testing is initiated.

Having herein described a preferred embodiment of the present invention, it is anticipated that suitable modifications may be made thereto by individuals skilled in the art within the scope of the invention, including but not limited to dimensional and configurational alterations. Accordingly, the invention shall only be construed in connection with the following claims.

What is claimed is:

1. An apparatus for preserving and testing a cornea-containing tissue specimen comprising:
    a chamber having a top portion, a bottom portion, and a medial portion between said top portion and said bottom portion, said medial portion having at least one side wall portion, said side wall portion having a port therethrough;
    a downwardly extending cover member operatively secured to said chamber and positioned over said port, said cover member being comprised of a non-abrasive material which is biologically compatible with said cornea-containing tissue specimen; and
    nutrient supply means operatively attached to said chamber for delivering liquid nutrient materials onto said cover member.

2. The apparatus of claim 1 wherein said top portion of said chamber comprises an opening therethrough, and a sealing member detachably secured to said opening.

3. The apparatus of claim 1 wherein said top portion comprises a first bore therethrough sized to receive a thermometer.

4. The apparatus of claim 3 wherein said tip portion further comprises a second bore therethrough sized to receive at least one heating unit.

5. The apparatus of claim 1 wherein said cover member comprises a material selected from the group consisting of omentum tissue, conjunctival tissue, and species-specific fibroblastic monolayer tissue.

6. The apparatus of claim 1 further comprising attachment means for securing the cornea-containing tissue specimen to said side wall portion of said chamber over said port.

7. The apparatus of claim 6 wherein said attachment means further comprises an annular flange extending outwardly from said port, wherein the cornea-containing tissue specimen will be positioned on top of and secured to said flange during the use of said apparatus.

8. The apparatus of claim 7 further comprising a cornea retaining ring sized to securely fit over said flange, wherein the cornea-containing tissue specimen will be fixedly positioned between said ring and said flange during the use of said apparatus in order to retain said specimen in position.

9. The apparatus of claim 1 wherein said cover member comprises an upper edge and a lower edge, and said nutrient supply means comprises a nutrient supply conduit operatively secured to said chamber adjacent said upper edge of said cover member, said nutrient supply means further comprising an external source of liquid nutrient materials in fluid communication with said nutrient supply conduit, said external source of liquid nutrient materials and said nutrient supply conduit delivering said liquid nutrient materials to said cover member.

10. The apparatus of claim 9 wherein said nutrient supply conduit comprises a first end and a second end, said first end being in fluid communication with said external source of liquid nutrient materials, and said second end being operatively secured to said chamber adjacent said upper edge of said cover member, said second end further comprising a plurality of perforations therethrough.

11. The apparatus of claim 1 further comprising waste collection means for receiving excess, residual amounts of said liquid nutrient materials which drain off of the cover member during the use of said apparatus.

12. The apparatus of claim 11 wherein said waste collection means comprises an elongate reservoir secured to said chamber beneath said port and beneath a lower edge of said cover member, said reservoir receiving said residual amounts of said liquid nutrient materials from said cover member.

13. The apparatus of claim 12 wherein said waste collection means further comprises a waste conduit secured to said reservoir for directing said residual amounts of said liquid nutrient materials out of said reservoir.

14. An apparatus for preserving and testing a cornea-containing tissue specimen comprising:
   a chamber having a top portion, a bottom portion, and a medial portion between said top portion and said bottom portion, said medial portion having at least one side wall portion, said side wall portion having a port therethrough;
   attachment means for securing the cornea-containing tissue specimen to said side wall portion of said chamber over said port;
   a cover member operatively secured to said chamber and positioned over said port, said cover member having an upper edge and a lower edge, said cover member being comprised of a non-abrasive material which is biologically compatible with said cornea-containing tissue specimen;
   nutrient supply means operatively attached to said chamber for delivering liquid nutrient materials onto said cover member comprising a nutrient supply conduit operatively secured to said chamber adjacent said upper edge of said cover member, said nutrient supply means further comprising an external source of liquid nutrient materials in fluid communication with said nutrient supply conduit, said external source of liquid nutrient materials and said nutrient supply conduit delivering said liquid nutrient materials to said cover member; and
   waste collection means for receiving excess, residual amounts of said liquid nutrient materials which drain off of said cover member during the use of said apparatus, said waste collection means comprising a reservoir secured to said chamber beneath said port and beneath said lower edge of said cover member, said reservoir receiving said residual amounts of said liquid nutrient materials from said cover member.

15. An apparatus for preserving and testing a cornea-containing tissue specimen comprising:
   a chamber having a top portion, a bottom portion, and a medial portion between said top portion and said bottom portion, said top portion comprising an opening therethrough, a sealing member detachably secured to said opening, a first bore therethrough sized to receive a thermometer, and a second bore therethrough sized to receive at least one heating unit;
   said medial portion comprising a port therethrough, said port further comprising an annular flange extending outwardly therefrom, so that the specimen will be positioned on top of and secured to said flange during the use of said apparatus;
   a cornea retaining ring sized securely to fit over said flange so that the cornea-containing tissue specimen will be fixedly positioned between said ring and said flange during the use of said apparatus in order to retain the specimen in position;
   a cover member operatively secured to said chamber and positioned over said port, said cover member comprising an upper edge and a lower edge;
   nutrient supply means operatively attached to said chamber for delivering liquid nutrient materials onto said cover member comprising a nutrient supply conduit operatively secured to said chamber adjacent said upper edge of said cover member, said nutrient supply means further comprising an external source of liquid nutrient materials in fluid communication with said nutrient supply conduit, said external source of liquid nutrient materials and said nutrient supply conduit delivering said liquid nutrient materials to said cover member; and
   waste collection means for receiving excess, residual amounts of said liquid nutrient materials which drain off of said cover member during the use of said apparatus, said waste collection means comprising an elongate reservoir secured to said chamber beneath said port and beneath said lower edge of said cover member, said reservoir receiving said residual amounts of said liquid nutrient materials from said cover member, said waste collection means further comprising a waste conduit secured to said reservoir for directing said residual amounts of said liquid nutrient materials out of said reservoir.

* * * * *